United States Patent [19]

Chafin et al.

[11] Patent Number: 4,754,040

[45] Date of Patent: Jun. 28, 1988

[54] METHOD OF PREPARING AN EXPLOSIVE COMPOUND

[75] Inventors: Andrew P. Chafin, Levittown, Pa.; Ronald L. Atkins, Ridgecrest, Calif.

[73] Assignee: The United States of America as represented by the Secretary of the Navy, Washington, D.C.

[21] Appl. No.: 731,074

[22] Filed: Feb. 25, 1985

[51] Int. Cl.$^4$ ............................................. C07D 271/12
[52] U.S. Cl. ............................................................ 548/126
[58] Field of Search ............................................ 548/126

[56] References Cited

U.S. PATENT DOCUMENTS

| | | | |
|---|---|---|---|
| 4,185,018 | 1/1980 | Fäh | 548/126 |
| 4,217,356 | 8/1980 | Neumann | 548/126 |
| 4,529,801 | 7/1985 | Norris | 548/126 |

FOREIGN PATENT DOCUMENTS

| | | | |
|---|---|---|---|
| 1210604 | 10/1970 | United Kingdom | 548/126 |
| 627129 | 10/1978 | U.S.S.R. | 548/126 |
| 657025 | 4/1979 | U.S.S.R. | 548/126 |

OTHER PUBLICATIONS

Boulton et al, *J. Chem. Soc.* (B), 1967, pp. 909–911.

*Primary Examiner*—Edward A. Miller
*Attorney, Agent, or Firm*—W. C. Townsend; W. Thom Skeer; Stephen J. Church

[57] ABSTRACT

A method of preparing 4,6-dinitro-5,7-diaminobenzofuroxan from 4,6-dichlorobenzofuroxan.

7 Claims, No Drawings

METHOD OF PREPARING AN EXPLOSIVE COMPOUND

BACKGROUND OF THE INVENTION

1. Field of the Invention

This invention relates to explosives. More specifically, this invention relates to a method of preparing 4,6-dinitro-5,7-diaminobenzofuroxan, a compound useful as an explosive.

2. Description of the Prior Art

Organic chemical compounds which contain nitro groups are well known as explosives. Typical examples are trinitrotoluene (TNT) and triaminotrinitrobenzene (TATB).

Despite the availability of many explosive nitro containing organic compounds, the search for new ones with improved properties continues. The compound described herein, 4,6-dinitro-5,7-diaminobenzofuroxan, was first synthesized in Norris, Ser. No. 259,203, filed on April 13, 1981. This invention provides an improved method of preparing said compound, giving a higher yield, and utilizing more readily available starting materials.

SUMMARY OF THE INVENTION

This invention provides a method of preparing an insensitive, high density explosive that is more powerful than triaminotrinitrobezene. The explosive 4,6-dinitro-5,7-diaminobenzofuroxan is prepared by a five step process using orthonitroaniline as the starting material.

DESCRIPTION OF THE PREFERRED EMBODIMENT

The starting material used is orthonitroaniline. This is chlorinated to yield 2,4-dichloro-6-nitroaniline by the method described in Y. E. Gerasimenko et al., *Zh. Prikl. Khim.* 39, p. 1677 (1966) with the exception that no dispersing agent is used. The 2,4-dichloro-6-nitroaniline is then dissolved in hydrochloric acid and $NaNO_2$ is added. The unreacted 2,4-dichloro-6-nitroaniline is recovered by filtration and $NaN_3$ is added to the filtrate to yield 2,4-dichloro-6-nitroazidobenzene.

The compound 2,4-dichloro-6-nitroazidobenzene is dissolved in glacial acetic acid then refluxed for several hours to yield 4,6-dichlorobenzofuroxan. This step is similar to that described in Boulton et al., *J. Chem. Soc. B.*, p. 909 (1967) except that the present invention uses a longer reflux time.

A nitric acid-oleum mixture is made, to which is added 4,6-dichlorobenzofuroxan. Subsequently, $H_2SO_4$ is added and the mixture extracted with methylene chloride. The methylene chloride solutions are treated with magnesium sulfate, filtered, and the solvent removed to yield 4,6-dinitro-5,7-dichlorobenzofuroxan.

The compound 4,6-dinitro-5,7-dichlorobenzofuroxan is then dissolved in ethylene chloride. Ammonia gas is passed over the solution until no more gas is absorbed. Upon removal of the solvent the ammonium salt of 4,6-dinitro-5,7-diaminobenzofuroxan and ammonium chloride remain as a powder. This is washed with HCl and filtered to yield the desired product 4,6-dinitro-5,7-diaminobenzofuroxan.

The preferred embodiment of this invention may be further understood by referring to the following specific example.

EXAMPLE

The starting material orthonitroaniline is chlorinated to yield 2,4-dichloro-6-nitroaniline (93% yield).

A mixture is made of 5.00 g (24.2 mmol) 2,4-dichloro-6-nitroaniline dissolved in 75 ml of concentrated HCl. The temperature is maintained at a level below 5° C. with an ice bath and 1.83 g (26.5 mmol, 1.1 eq.) of $NaNO_2$ in 15 ml of water is added dropwise. After one hour of stirring below 5° C., the mixture is filtered and 0.53 g (10.6% yield) of 2,4-dichloro-6-nitroaniline is recovered. The filtrate composes a solution of 2,4-dichloro-6-nitrodiazobenzene. The solution temperature is maintained below 5° C. while a solution of 1.73 g (26.6 mmol, 1.1 eq.) $NaN_3$ in 15 ml of water is added dropwise. The compound 2,4-dichloro-6-nitroazidobenzene is filtered off and washed with water. The yield is 4.66 g (82.8%) and the compound has a melting point of 42 to 42.5° C. The total yield including recovered 2,4-dichloro-6-nitroaniline is 93.4%.

A mixture of 0.63 g (2.7 mmol) of 2,4-dichloro-6-nitroazidobenzene and 25 ml glacial acetic acid is made and is refluxed for three to six hours. This is then poured over ice water, filtered and washed with water to yield 0.51 g (92.1% yield) of 4,6-dichlorobenzofuroxan, having a melting point of 105 to 105.5° C. Experimental runs result in yields ranging from 75 to 92%. The material can be recrystallized from ethanol/water if desired.

A mixture is then made of 15 ml of 90% $HNO_3$ ($\approx 300$ mmol, 15 eq.) and 180 ml of 22% oleum. This mixture is cooled in an ice bath to around 10° C. and 4.10 g (20 mmol) of 4,6-dichlorobenzofuroxan is added over a period of five minutes. The mixture is then heated to 50° C., maintained at that temperature for 3.5 hours and then cooled to 10° C. To this, 200 ml of 96% $H_2SO_4$ is added and the mixture extracted with three 330 ml portions of methylene chloride. The methylene chloride solution is treated with magnesium sulfate, filtered, and the solvent removed in vacuum to give 4,6-dinitro-5,7-dichlorobenzofuroxan. The yield is 4.86 g (82.4%). This compound may be recrystallized from 1200 ml hexane, if desired.

The compound 4,6-dinitro-5,7-dichlorobenzofuroxan (2.00 g, 6.8 mmol) is dissolved in 50 ml of ethylene chloride. Ammonia is slowly passed over the stirred solution until no more gas is absorbed (about 1.5 hours). The solvent is then removed in vacuum. The remaining powder (2.65 g) is the ammonium salt of 4,6-dinitro-5,7-diaminobenzofuroxan and ammonium chloride. This powder is stirred with 50 ml of 50% by volume HCl overnight. The mixture is filtered and the yellow powder is washed well with water to yield 1.64 g (94.2% yield) of 4,6-dinitro-5,7-diaminobenzofuroxan.

This invention has been described in detail with particular reference to certain preferred embodiments thereof, but it will be understood that variations and modifications can be effected within the spirit and scope of the invention.

What is claimed is:

1. A method of making 4,6-dinitro-5,7-diaminobenzofuroxan comprising the steps of:
   A. reacting 4,6-dichlorobenzofuroxan with a mixture of nitric acid and sulfuric acid to obtain 4,6-dinitro-5,7-dichlorobenzofuroxan;
   B. reacting said 4,6-dinitro-5,7-dichlorobenzofuroxan with ammonia gas to obtain a powder; and
   C. stirring said powder with hydrochloric acid to produce 4,6-dinitro-5,7-diaminobenzofuroxan.

2. The method of claim 1 wherein step A is carried on by adding 4,6-dichlorobenzofuroxan to a mixture of 90% HNO$_3$ and 22% oleum.

3. The method of claim 1 wherein said sulfuric acid of step A is 96% H$_2$SO$_4$.

4. The method of claim 1 wherein the said reaction mixture of step A is extracted with methylene chloride and subsequently treated with magnesium sulfate.

5. The method of claim 1 wherein step B is carried on by dissolving said 4,6-dinitro-5,7-dichlorobenzofuroxan in ethylene chloride to form a solution.

6. The method of claim 5 wherein ammonia is passed over said solution.

7. The method of claim 1 wherein said hydrochloric acid of step C is 50% by volume HCl.

* * * * *